United States Patent [19]

Link et al.

[11] 4,174,707

[45] Nov. 20, 1979

[54] APPARATUS AND PROCESS FOR ANTIFACT REJECTION THROUGH CROSS CORRELATION IN SPHYGMOMETRY

[75] Inventors: William T. Link, Berkeley; Jerry D. Haney, Sunnyvale; William D. Jansen, Palo Alto, all of Calif.

[73] Assignee: American Optical Corporation, Southbridge, Mass.

[21] Appl. No.: 754,200

[22] Filed: Dec. 27, 1976

[51] Int. Cl.$^2$ ............................................. A61B 5/02
[52] U.S. Cl. .............................................. 128/681
[58] Field of Search ............... 128/2.05 A, 2.05 C, 128/2.05 D, 2.05 E, 2.05 G, 2.05 M, 2.05 Z, 2.05 Q

[56] References Cited

U.S. PATENT DOCUMENTS

| | | | |
|---|---|---|---|
| 3,814,083 | 6/1974 | Fletcher et al. | 128/2.05 A |
| 3,878,833 | 4/1975 | Arneson et al. | 128/2.05 A |
| 3,903,872 | 9/1975 | Link | 128/2.05 A |
| 4,001,461 | 12/1976 | Barber et al. | 128/2.05 A X |
| 4,009,709 | 3/1977 | Link et al. | 128/2.05 A |
| 4,027,662 | 6/1977 | Lee | 128/2.05 A |
| 4,030,485 | 6/1977 | Warner | 128/2.05 A |
| 4,078,551 | 3/1978 | Wohltjen et al. | 128/2.05 M |

OTHER PUBLICATIONS

Chungeharoen, D., "Genesis of Korotkov Sounds", Amer. Jrnl Physiology, v. 207, No. 1, Jul. 1964, pp. 190-194.
Randall, M. J. et al., "Computer Automation of Blood Pressure Measurements", Proc. of IEEE, v. 63, #10, Oct. 1975, pp. 1399-1403.
Schulze, A. E. et al., "A System for Automatic Measurement of Systolic and Diastolic Blood Pressures", Southwestern IEEE Conf. Records, Apr. 1968, pp. 17F1-17F5.

Primary Examiner—Robert W. Michell
Assistant Examiner—Francis J. Jaworski
Attorney, Agent, or Firm—Jeremiah J. Duggan; Alan H. Spencer; Stephen A. Schneeberger

[57] ABSTRACT

In a system for measuring blood pressure and the like based on a sensed quantity representing the sum of pressure applied by a pressure cuff and a fluctuating component representative of the pulsatile pressure within the blood vessel method and apparatus for indicating blood pressure only if that pressure determined in a first preferred manner correlates substantially with a pressure determined in a secondary, different manner. More specifically, the sensed quantity is analyzed in a manner preferred for determining diastolic pressure and a manner preferred for determining systolic pressure, and the diastolic and systolic pressures or pressure ranges established by analyzing the sensed quantity in a secondary manner or manners. Examples of preferred and secondary techniques for diastolic and systolic pressure determinations are discussed.

22 Claims, 8 Drawing Figures

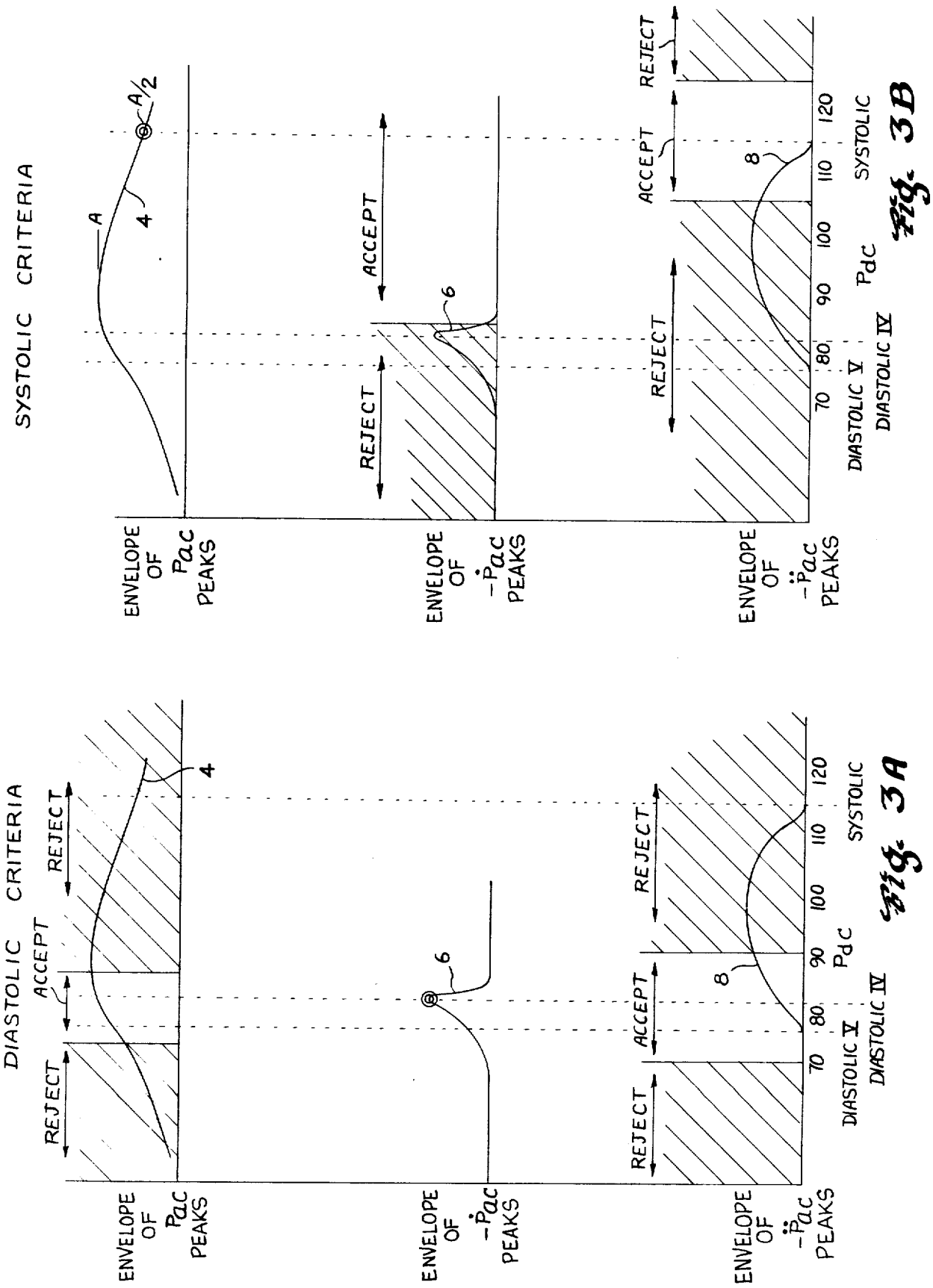

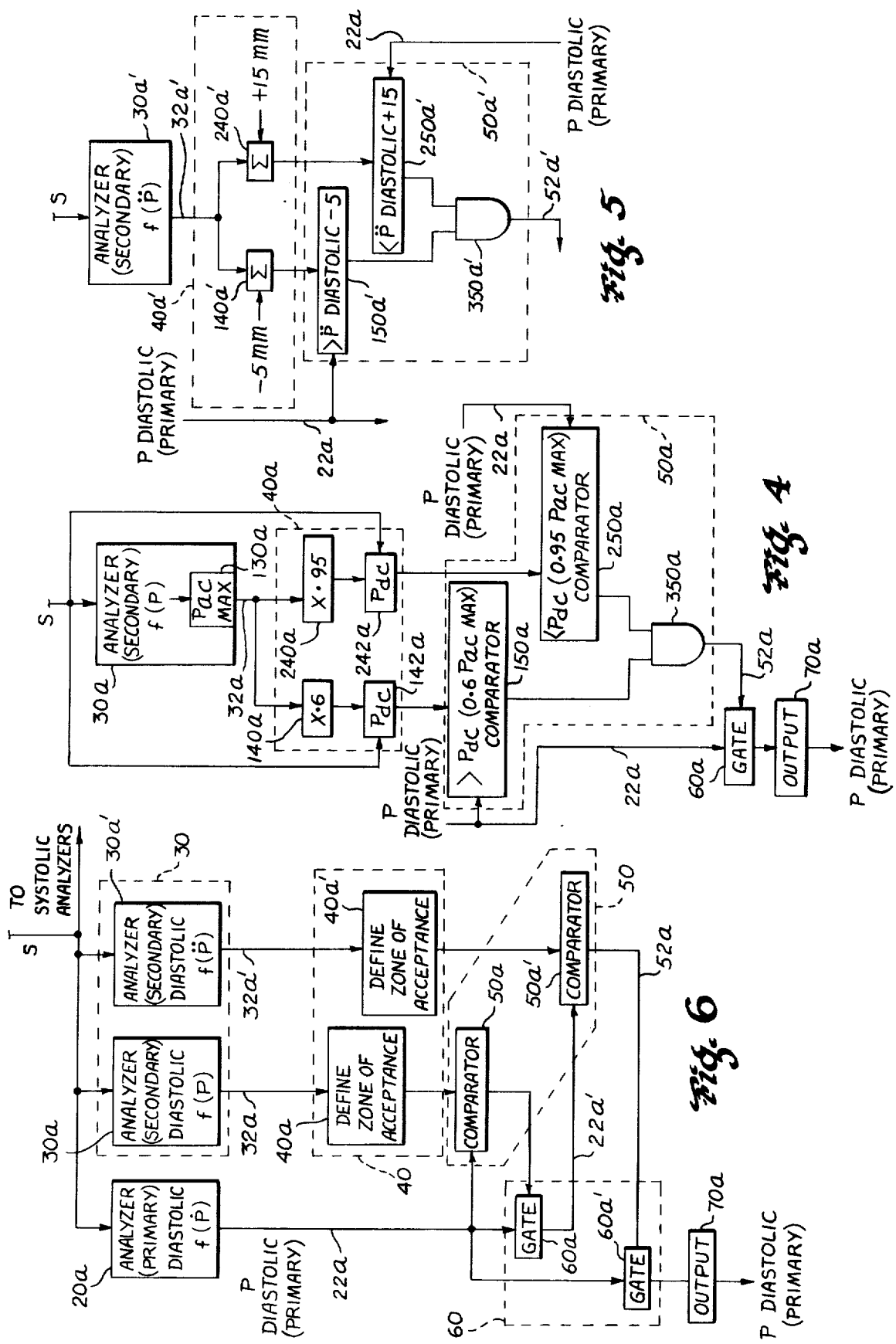

APPARATUS AND PROCESS FOR ANTIFACT REJECTION THROUGH CROSS CORRELATION IN SPHYGMOMETRY

BACKGROUND OF THE INVENTION

The present invention relates generally to the field of sphygmometry, and moe particularly to sphygmometric blood pressure monitoring.

The prior art is replete with devices for measuring the blood pressure of a living subject. An old and simple device is a pressurizable cuff used in combination with a mercury manometer which reads pressure in the cuff and a stethoscope which is used to listen to Korotkoff sounds. More complicated methods and apparatus based on the same principle of listening to the Korotkoff sounds replace the mercury manometer with a mechanical or electromechanical pressure gauge and utilize microphonic detection of the Korotkoff sounds which are analyzed electrically. In another advanced method for measuring blood pressure, the distance from a blood pressure cuff to the wall of an artery is accurately determined by measuring Doppler shifts of sound waves reflected by the artery. The distance to the artery varies as a function of pressure within the somewhat pliable walls thereof. In yet other methods for measuring blood pressure intrusive devices may be inserted directly into the blood vessels.

Oscillometric methods of determining blood pressure are also known in the art. Several recent contributions to the art of oscillometric blood pressure monitoring have been provided by one or more of the present inventors as represented by U.S. Pat. No. 3,903,872 issued to William T. Link on Sept. 9, 1975 for Apparatus and Process for Producing Sphygmometric Information; U.S. application Ser. No. 578,047 filed May 15, 1975 by Link et al for Apparatus and Process for Determining Systolic Pressure and now U.S. Pat. No. 4,009,709; and more recently U.S. application Ser. No. 754,133, filed Dec. 27, 1976, by William T. Link for Apparatus and Process Using Second Derivative of Oscillometric Waveform for Producing Sphygmometric Information, each of the aforementioned patents and/or applications being incorporated herein by reference.

The U.S. Pat. No. 3,903,872 discloses a technique and apparatus for the accurate determination of diastolic blood pressure by employing an oscillometric technique in which a pulsating signal derived from a pressurizable cuff is differentiated to provide a first time derivative ($\dot{P}_{ac}$), which first time derivative is then maximized as a function of the applied pressure to obtain diastolic pressure.

The U.S. application Ser. No. 578,047 now U.S. Pat. No. 4,009,709 discloses a relationship between the length of the pressure cuff and that portion of an embraced blood vessel which undergoes volumetric change at systolic pressure, such as to permit a fairly accurate determination of systolic pressure to be made as a function of the amplitude of the pulsatile pressure sensed in the cuff. In the normally encountered situation the systolic pressure is recognized as that at which the amplitude of the pulsating component ($P_{ac}$) of pressure sensed in the pressurized cuff is about ½ the maximum pulse amplitude for an applied pressure greater than the pressure at which the maximum pulsatile pressure occurs.

In addition to utilizing the maximized negative first time derivative of the pulsatile pressure to establish the diastolic pressure of a blood vessel, it is further appreciated that the applied pressure region above the diastolic pressure necessarily embraces the systolic pressure and may be considered to be a nonspecific indicator of the range in which the systolic pressure may be found. Further, analysis of the amplitude of the pulsatile pressure as the applied pressure is varied at least across the diastolic-systolic range, in addition to revealing the systolic pressure, may also be utilized to generally indicate a range for the diastolic pressure which corresponds with the "left-hand shoulder" of the envelope which embraces the plot of the pulse pressure waveform across the applied pressure range.

In the aforementioned application Ser. No. 754,133 by Link, there is disclosed an alternative technique for determining both diastolic and systolic pressure. This technique utilizes the second time derivative ($\ddot{P}_{ac}$) of the sensed pulsatile pressure by noting when negative spikes of the second time derivative first and last exceed some minimal negative threshold level as applied cuff pressure is differed across the diastolicsystolic range. The applied pressures corresponding with the onset and termination of such threshold-exceeding negative second time derivative signals correspond substantially with diastolic and systolic pressures of the blood vessel.

However, in essentially all of the preceding techniques (including oscillometry) for measuring blood pressure, including invasive techniques, there exists the problem that signal artifacts arising from random muscular activity and the like may result in inaccurate or invalid pressure readings. A variety of techniques have been employed for rejecting artifacts from the sensed signal in an effort to improve the accuracy of the various equipment. For instance, such techniques have rejected pulses of too great or too small amplitude, and/or pulses which occur too early or too late relative to some time reference. Further, several pulses may be averaged so that the effect of any artifact is decreased. Further still, the blood pressure waveforms used in oscillometric techniques may be correlated with waveforms obtained from an electrocardiographic analysis in an effort to reject artifact signals. Although the foregoing artifact rejection and/or moderation techniques contribute to increased accuracy in blood pressure monitoring equipment, they may be expensive to employ and/or certain artifacts may in any event continue to appear.

Accordingly, it is a principle object of the invention to provide improved apparatus and process for identifying and/or rejecting artifacts in blood pressure measurements.

SUMMARY OF THE INVENTION

The apparatus and process of the invention provide improved accuracy in the output statement from equipment measuring the physical condition of a living test subject. More specifically, the invention provides for artifact recognition and/or rejection through the application of cross-correlation techniques. The invention is specifically applicable to the provision of improved measurements from blood pressure measuring equipment, and particularly such equipment utilizing oscillometric analytical techniques though not limited thereto.

The invention is further based on the premise that it is preferable to identify and generally suppress or abort a blood pressure measurement which is invalid due to artifact or the like, rather than to display such measurement. Were such invalid measurement displayed it might be incorrectly assumed as valid or alternatively, the error of the resulting measurement may be so great as to be considered absurd and thereby damage the credibility of the instrument. Thus, the present invention finds its greatest utility as a supplement to various of the aforementioned other artifact suppression techniques.

In one sense, the invention comprises an apparatus for producing information indicative of the physical condition of a living test subject, which apparatus comprises means for applying a selectively changeable pressure to the test subject adjacent a blood vessel and means for measuring a fluctuating quantity proportional to a sum, the sum comprising a time dependent fluctuating component representative of the pulsatile pressure within the blood vessel, plus the selectively changeable pressure applied externally adjacent the blood vessel; first means responsive to the quantity in a first analytical manner for providing at least one primary signal tentatively representative of the physical condition of the living test subject; second means responsive to the quantity in the second analytical manner different from the first analytical manner for defining at least one respective zone of acceptance expressed in terms of the test subject physical condition; and means for comparing a primary signal with the respective zone of acceptance and producing an output of the primary signal as being representative of the physical condition of the living test subject only if the primary signal is within a respective zone of acceptance.

In another sense the invention comprises a process for producing information indicative of the physical condition of the living test subject comprising applying a selectively changeable pressure to the test subject externally adjacent the blood vessel and measuring a quantity proportional to a sum, the sum comprising a time dependent fluctuating component representative of the pulsatile pressure within the blood vessel plus the changeable pressure applied externally adjacent the blood vessel; analyzing the quantity in a first manner to provide at least one primary signal tentatively representative of the physical condition of a living test subject; analyzing the quantity in a second manner different from the first analytical manner to define at least one respective zone of acceptance expressed in terms of the test subject physical condition; and comparing the primary signal with the respective zone of acceptance and providing an output of the primary signal as being representative of the physical condition of a living test subject only if the primary signal is within the respective zone of acceptance.

As earlier mentioned, several different analytical techniques have been developed for the determination of systolic and/or diastolic pressure of a blood vessel. One or more of these techniques may provide a respective diastolic or systolic blood pressure with a relatively high degree of accuracy; whereas one or more of the other techniques may identify a systolic or diastolic pressure with a somewhat lesser degree of accuracy or specificity. Accordingly, the invention utilizes one of the more accurate analytical techniques in deriving a primary signal tentatively representative of either diastolic or systolic pressure and utilizes one or more different secondary analytical techniques to define so-called zones-of-acceptance into which the respective primary signal should fall if it indeed is a valid diastolic or systolic measurement. In this way, a signal analysis technique which may result in a particularly accurate and specific indication of diastolic or systolic pressure, but which is also somewhat prone to artifact interference, may be corroborated through cross-correlation with a zone-of-acceptance defined by a corresponding diastolic or systolic pressure determined by a second analytical technique different than the first and which may be less prone to the particular artifact problems of the first analytical technique. Further, such cross-correlation tends to isolate those artifacts which are generated during signal processing in the respective analytical systems themselves.

Preferably a defined zone-of-acceptance is of greater breadth than the pressure value comprising the primary signal.

In one embodiment, there may be two or more different secondary analytical techniques for obtaining two or more respective secondary signals for the purpose of defining respective zones-of-acceptance with which the primary signal is subsequently compared. In such arrangement, the primary signal may be read out or displayed at the system output if it at least lies within any one of the defined zones-of-acceptance or preferably, is read out only if it is in correlation with each of the zones-of-acceptance.

In a preferred embodiment, a primary diastolic pressure signal is provided by maximization of the negative of the first time derivative ($\dot{P}_{ac}$) of the sensed pulsating cuff pressure signal as a function of that cuff pressure signal, the primary systolic pressure signal being determined to be that applied pressure at which the sensed pulsating pressure ($P_{ac}$) is substantially one half of the maximum pulsating pressure at an applied pressure greater than that at which the pulsating pressure is a maximum. Further, the secondary signals for defining the zones-of-acceptance may be determined by further utilization of the f(P) and f($\dot{P}$) techniques. Alternatively or additionally, further secondary signals for defining respective zones of acceptance may be determined by utilizing the f($\ddot{P}$) technique of the aforementioned Link patent application which identifies diastolic and systolic pressures through use of the negative second derivative of the pulsatile pressure. In the above and further below, the form f($\chi$) is used to designate function of $\chi$ in the usual mathematical symbolism.

BRIEF DESCRIPTION OF THE DRAWINGS

FIG. 3A illustrates the diastolic criteria superimposed on the waveform envelopes associated with P, $\dot{P}$, and $\ddot{P}$ of FIG. 2;

FIG. 3B illustrates the systolic criteria superimposed on the waveform envelopes associated with P, $\dot{P}$ and $\ddot{P}$ of FIG. 2;

FIG. 4 is a block diagram illustrating a portion of FIG. 1 in greater detail;

FIG. 5 is a block diagram similar in form to that of FIG. 4 but comprising an alternative or supplement thereto;

FIG. 6 illustrates a detailed block diagram of a portion of the system illustrated in FIG. 1 to show the use of two different secondary analytical techniques;

FIG. 7 illustrates a detailed block diagram of the signal processing portion of FIG. 1 to show the use of primary diastolic and systolic signals and secondary diastolic and systolic signals.

Figure 1:
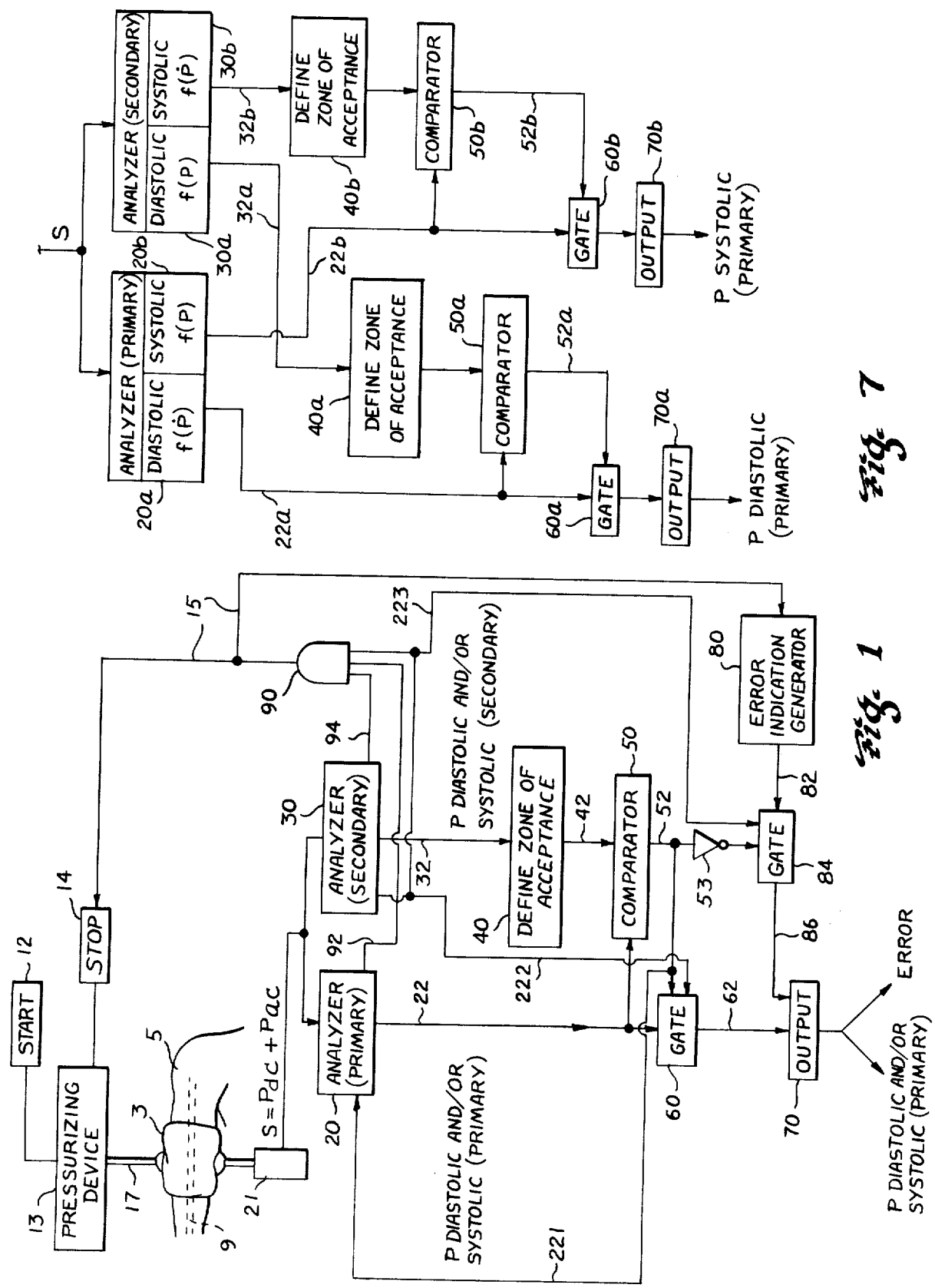
FIG. 1 is a generalized block diagram illustrating the apparatus and process of the present invention in combination with blood pressure monitoring equipment.

Referring now to the Figures and in particular initially to FIG. 1, the peferred embodiments of the invention can be better understood. Means for applying a differable pressure adjacent the blood vessel, said pressure for applying means comprising a blood pressure measuring means in particular a cuff 3 is shown in position about an arm 5 containing an artery 9 therein. The cuff 3 can be a typical blood pressure cuff such as those utilized when one is making use of a stethoscope to hear Korotkoff sounds. Also a part of said pressure applying means along with the cuff is the pump or pressurizing device 13, which can be a simple squeeze bulb or it can be a powered pump, acting through the tubing 17. As illustrated, device 13 comprises a powered pump, with pressurizing operation being initiated by actuation of start switch 12 and being terminated by manual or automatic actuation of stop switch 14. Automatic actuation of stop switch 14 may be provided by a signal on line 15 appearing at a predetermined pressure level or when sufficient data has been collected for determination of a patient's diastolic and systolic pressures.

The pressure resulting in the cuff 3 is the sum of the differable pressure supplied by the pressurizing device 13 and a pulsating pressure due to the time-dependent pulsatile pressure surges within the artery, this sum represented as S in FIG. 1. The cuff pressure is measured by the pressure transducer 21 or by other convenient means. Although the signal S from transducer 21 comprises a sum of the applied pressure and the pulsatile pressure, it should be noted that the applied pressure (designated $P_{dc}$) is many times greater than the pulsatile pressure (designated $P_{ac}$) and accordingly the value of S is substantially equal to the pressure $P_{dc}$ applied by cuff 3.

The output S of the pressure transducer 21 may pass through a preamplifier, not shown, and is then extended to the appropriate input or inputs of primary analyzer 20 and secondary analyzer 30. Although the analyzers 20 and 30 may be constructed of discrete analog and/or digital circuits, the use of one or more microprocessors is contemplated in the preferred embodiment to provide for the function of not only analyzers 20 and 30 but also some of the logic circuitry subsequent thereto. The following discussion of primary and secondary analyzers 20 and 30 will be principally of a functional nature, but further detail thereof may be obtained from the disclosures contained in the three aforementioned U.S. Patents and/or Applications incorporated herein by reference. Primary and secondary analyzers 20 and 30 respectively provide output signals 22 and 32 which are each respectively indicative of a determined diastolic and/or systolic pressure. For instance, if the signal appearing on line 22 is representative of a diastolic pressure, the corresponding signal on line 32 will also be representative of a diastolic pressure. Alternatively, lines 22 and 32 may each bear indications of systolic pressure or, in the usual case indications of both diastolic and systolic pressure to be hereinafter described.

It is basic to the invention that the analytical technique for obtaining the diastolic and/or systolic pressure 22 from primary analyzer 20 is different that the analytical technique employed by analyzer 30 in deriving the respective diastolic and/or systolic pressure signal 32. It is appropriate at this juncture to consider several different analytical techniques for the determination of diastolic and systolic pressure, with particular reference to the waveforms of FIGS. 2, 3A and 3B. Although the invention is not limited to use of the three following described analytical techniques, such techniques do comprise the basis for one or more preferred embodiments to be hereinafter described.

Figure 2:
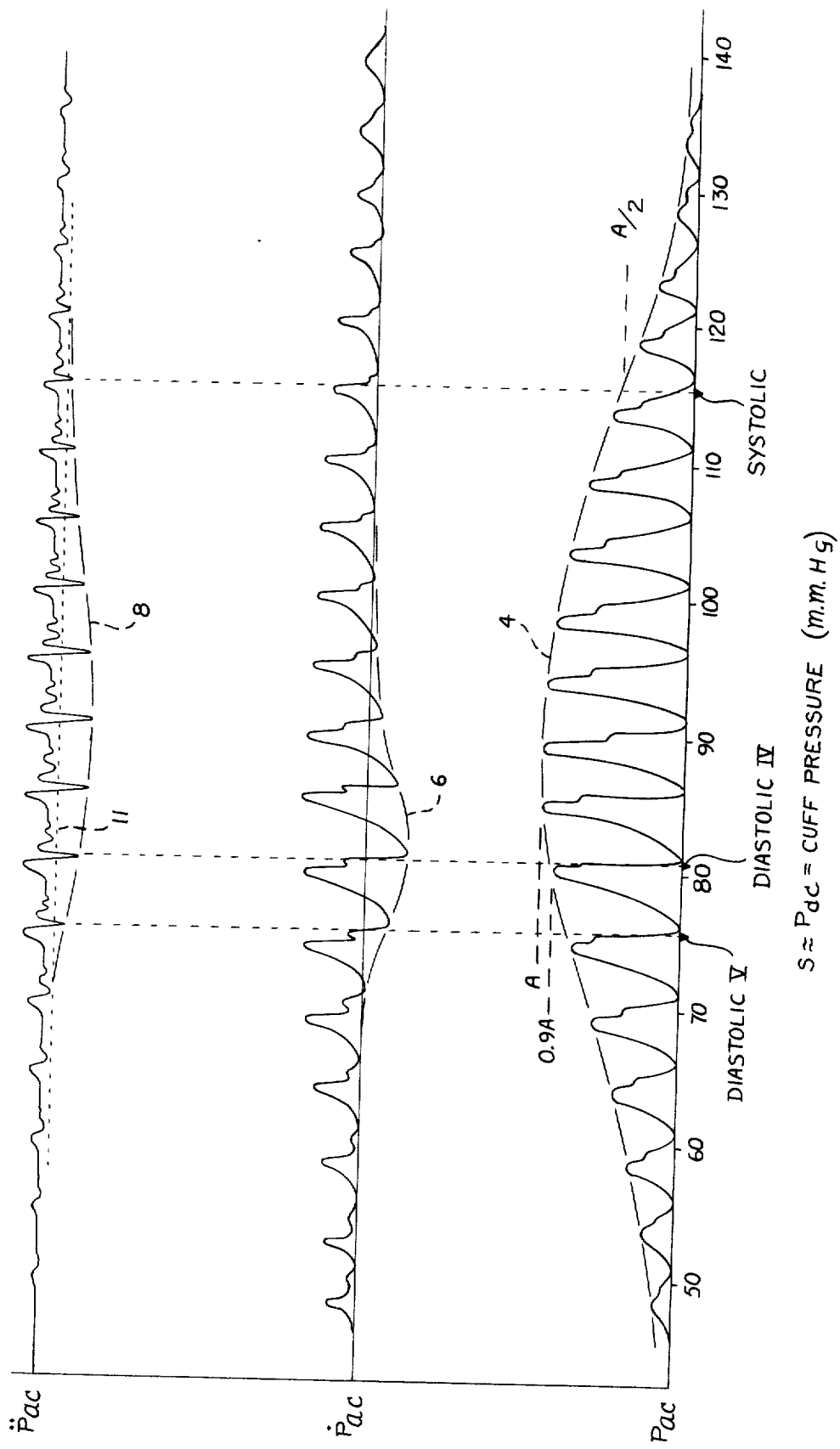
FIG. 2 illustrates the $P_{ac}$, $\dot{P}_{ac}$, and $\ddot{P}_{ac}$, or so called P, $\dot{P}$ and $\ddot{P}$ waveforms as the applied cuff pressure is differed.

Referring to FIG. 2, there are illustrated the signal waveforms of the $P_{ac}$ component of the output S of pressure transducer 21, the $\dot{P}_{ac}$ first time derivative of the $P_{ac}$ signal and the $\ddot{P}_{ac}$ second time derivative of the $P_{ac}$ signal, each appearing as a function of the applied cuff pressure $P_{dc}$ which is substantially equal to the output S from transducer 21. The correlation of the analytical techniques expressed in FIGS. 2, 3A and 3B with the measurement of Korotkoff sounds is expressed by the indicia DIASTOLIC V, DIASTOLIC IV and SYSTOLIC appearing along the baseline of the waveform representations. Thus, in the illustrated exemplary situation and using conventional auscultatory techniques, the patient's systolic pressure would appear to be about 115 mm Hg and his diastolic pressure (fifth phase) would be about 75 mm Hg.

Inasmuch as the amplitudes of the $P_{ac}$, $\dot{P}_{ac}$, and $\ddot{P}_{ac}$ signals provide the basis in the main, for the determination of diastolic and systolic pressures, it is convenient for purposes of further illustration and discussion to illustrate the amplitude with the dotted line envelope 4 for the $P_{ac}$ waveform, envelope 6 for the $\dot{P}_{ac}$ waveform and envelope 8 for the $\ddot{P}_{ac}$ waveform.

Referring to the $P_{ac}$ waveform it will be noted that the respective pulses, and thus envelope 4, experience a maximum amplitude, represented by A, in part of the region between the diastolic and systolic pressures. Further, in accordance with the teaching of the aforementioned Link et al U.S. Patent application Ser. No. 578,047 now U.S. Pat. No. 4,009,709, it will be noted that the point at which the envelope 4 has an amplitude which is about ½ (i.e. A/2) that of the maximum amplitude and at a greater applied pressure than for the maximum amplitude A is representative of the patient's systolic pressure. Furthermore, it has been recognized that the diastolic pressure will occur in a region generally defined by the left-hand shoulder of the envelope 4.

Referring to the $\dot{P}_{ac}$ waveforms, it will be noted from envelope 6 that the negative amplitude of the first time derivative of the $P_{ac}$ waveform experiences a maximum, which maximum is here illustrated as occurring at about 80 mm Hg and which accurately corresponds with Korotkoff fourth phase diastolic pressure in accordance with the principles of U.S. Pat. No. 3,903,872. Further analysis of the $\dot{P}_{ac}$ first time derivative waveform at applied pressures above the diastolic pressure do not provide an accurate indication of systolic pressure. Accordingly, systolic pressure may only be presumed as being at an applied pressure greater than that occurring at the negative maximum representation of the diastolic pressure.

The plot of the $\ddot{P}_{ac}$ waveform, and more particularly the envelope 8 thereof, illustrates, in accordance with the teaching of the aforementioned Link Application, that the negative peaks of the waveform negatively exceed a minimum threshold 11 entirely and only over the region, between diastolic and systolic pressure. Accordingly, the onset and termination of such threshold-exceeding negative spikes are, to a close approximation, indicative of applied pressures corresponding with the patient's diastolic and systolic pressures.

Referring more particularly to FIGS. 3A and 3B, there are illustrated a preferred analytical technique for determining diastolic pressure, a preferred analytical technique for determining systolic pressure, and two alternate secondary techniques for generally each determining diastolic and systolic pressures. The preferred technique for the determination of diastolic pressure resides in the maximization of the negative $\dot{P}_{ac}$ signal and is represented in FIG. 3A by the doubly circled point corresponding with the pressure of about 80 mm Hg. The preferred technique for determining systolic pressure resides in determining the pressure at which the amplitude of the $P_{ac}$ waveform envelope 8 is about ½ that of the maximum amplitude at a pressure greater than that of which the maximum amplitude occurs. The systolic pressure so determined is represented by the doubly circled point on the $P_{ac}$ waveform under the systolic criteria of FIG. 3B and corresponds with an applied pressure of about 115 mm. Hg. The remaining criteria for the determination of diastolic and systolic pressures in FIGS. 3A and 3B are considered to be secondary.

The diastolic criteria employing the $P_{ac}$ waveform recognizes that the diastolic pressure lies in a region defined by the lefthand shoulder of the envelope 4. The diastolic pressure is presumably that at which the amplitude of envelope 4 at the lefthand shoulder is about 90% of the maximum amplitude, though this might vary upwardly by another 5% and downwardly by 30%, thereby defining a region between 0.6–0.95 maximum $P_{ac}$ amplitude. Alternatively, diastolic pressure might be considered as being within a range which is ±20 mm Hg about the applied pressure corresponding with 90% maximum $P_{ac}$. In the illustrated embodiment of FIG. 3A, the zone in which diastolic pressure is considered to possibly exist has been defined as the range (to the left of the maximum amplitude) which is between the amplitude of 0.6 and 0.95 $P_{ac}$ max. This zone has been termed the "acceptance zone", and the applied pressures above and below this zone-of-acceptance are considered as being in a rejection zone.

Referring to the $\dot{P}$ systolic criteria of FIG. 3B, it will be noted that the rejection zone includes the region of applied pressures below, including, and slightly above the diastolic pressure. Accordingly, the acceptance zone has been defined as that region of applied pressures beginning at about 5 or 10 mm above the diastolic pressure and extending indefinitely upwardly therefrom.

The diastolic criteria of FIG. 3A utilizing the $\dot{P}$ technique are seen to provide an acceptance zone for applied pressures beginning somewhat below and extending some distance above the applied pressure at which the envelope 8 first exceeds its minimum threshold value for an increasing applied pressure. This point of transition in the envelope 8 is representative of the Korotkoff fifth phase determination of diastolic pressure. Accordingly, the zone-of-acceptance is defined as extending downwardly for about 5 mm Hg and upwardly for about 15 mm Hg in order to easily encompass the Korotkoff fourth phase determination of diastolic pressure utilized by the $\ddot{P}_{ac}$ method. The applied pressures above and below this acceptance zone comprise rejection zones.

The systolic criterion of FIG. 3B utilizing the $\ddot{P}_{ac}$ technique of analysis also recognizes the point of transition of the envelope 8 between a zero and a non-zero magnitude value as being indicative of the systolic pressure and further defines the zone-of-acceptance to be that region of applied pressures extending ±10 mm Hg to either side of the transition pressure. Accordingly, the rejection zones comprise those applied pressures above and below the acceptance zone.

Referring back to FIG. 1 it will be appreciated that the pressure signal 22 will be representative of diastolic pressure as a function of $\dot{P}_{ac}$ and/or systolic pressure as a function of $\dot{P}_{ac}$. Furthermore, the pressure signal 32 may comprise diastolic pressure (s) determined as functions of $P_{ac}$ and/or $\dot{P}_{ac}$ respectively and may also include systolic pressure signals determined as functions of $\dot{P}_{ac}$ and/or $\ddot{P}_{ac}$ respectively.

Assuming for the moment that only a determination of diastolic pressure is being made, signal 22 will comprise a first diastolic pressure value and signal 32 will comprise a second value capable of use in defining the diastolic zone-of-acceptance. If signal 32 is the result of a $\dot{P}$ analysis, it will comprise a pressure value corresponding substantially with diastolic (fifth phase) pressure, however if the $P_{ac}$ diastolic criteria is used the signal 32 will normally comprise a representation of the maximum amplitude (A) of the signal envelope 4 for subsequent use in defining the zone-of-acceptance.

Similarly, should the signal 22 be representative of systolic pressure as a function of $P_{ac}$, the signal 32 might comprise a pressure value determined as a function of $\dot{P}$ which corresponds substantially with the systolic pressure, however if signal 32 is determined as a function of $\dot{P}$ it may be represented by the maximum of envelope 6 which corresponds with diastolic pressure for subsequent use in defining the systolic zone-of-acceptance referenced thereto.

The secondary signal 32 is extended to circuitry 40 for defining the zone-of-acceptance. Zone-of-acceptance circuitry 40 will normally comprise scaling and/or summing circuits as will be hereinafter evident following a discussion of FIGS. 4 and 5. Briefly, zone-of-acceptance circuitry 40 defines the limits of one or more zones-of-acceptance corresponding with the pressure signal appearing on line 22, which zone (s) of acceptance are extended to an input of comparator 50 via conductor means 42 illustrated as being a single line. The primary diastolic and/or systolic pressure signal 22 is applied to the other input of comparator 50 in order to determine whether or not it is within the zone-of-acceptance defined by circuit 40. The output of comparator 50 may normally be considered to be a logic zero in the absence of comparison between inputs 22 and 42, and to be unity or one when the signal on line 22 is within the zone-of-acceptance defined by the signal on line 42.

The signal on line 22 is further extended to an input of gate 60, with the output of comparator 50 being represented by line 52 and extended to the control input of gate 60. The logic of gate 60 is such that signal 22 is passed there through and via line 62 to output circuitry 70 only if the gate 60 is opened by a signal value of unity appearing on the output 52 of comparator 50. Thus it will be appreciated that the primary pressure value appearing on line 22 may be read-out from output device 70 only if it lies within the zone or range of acceptance defined by signal 42. The output 70 may comprise any sort of conventional readout or display means and may include storage registers for the retention of the pressure value (or values if both diastolic and systolic are determined) input thereto.

In the event the signal appearing on line 22 does not lie within the zone-of-acceptance defined by circuitry 40, it may be desirable to provide an output indication that an error has occurred, and possibly further, a statement of the nature of the error. To this end there is provided an error indication generator 80 which may provide a standard error signal or alternatively, a specific error signal as a function of a specific error, in response to an input signal thereto conveniently provided by the stop signal 15. The error indication signal represented by line 82 from generator 80 is extended to an input of gate 84 for selective extension via line 86 to the output circuitry 70. Gate 84 is controlled by comparator output signal 52 inverted by inverter 53 and extended to the control input of the gate. Thus, gates 60 and 84 function in a complementary manner such that either valid diastolic and/or systolic pressure measurements are read-out or an error indication is provided. A logic 0 from comparator 50, signaling that the diastolic or systolic pressure will be rejected, may be led back to the primary pressure determining device 20 via line 221 instructing it to attempt an alternative determination of pressure from the data which is still stored in it.

The pump-stopping signal 5, which may also serve to generate an indication of error, is provided whenever all of the data required for the diastolic and/or systolic pressure measurements have been obtained from both primary analyzer 20 and secondary analyzer 30. Normally, analyzers 20 and 30 extend respective end-of-run signals to the input of AND gate 90 via lines 92 and 94 respectively. The analyzers 20 and 30 may each be preprogrammed to generate respective end-of-run signals 92 and 94 at some predetermined setting of the applied pressure, or alternatively, they may generate such signals within a predetermined time or pressure following attainment of the last data required for the necessary pressure measurements. When both end-of-run signals 92 and 94 exist concurrently, AND gate 90 is operative to generate the stop and error indication signal 15 thereby discontinuing operation of pressurizing device 13 and generating an error indication 82 which may or may not subsequently be extended to the output 70. If secondary analyzer 30 is unable to determine a satisfactory measurement, it may deliver along lines 222 and 223 logical plus signals to output its data under the condition in which the secondary analyzer has failed. In other words, analyzer 30 may establish interval criteria for determining whether or not its output defines a valid zone-of-acceptance, as for instance by setting some minimum data requirement. If analyzer 30 determines its output to be incapable of defining a valid zone-of-acceptance, then it may output the signal on line 222 to gate 60 for outputting the data of the primary analyzer and the signal on line 223 may operate on gate 90 and/or gate 84 to also provide an "error" indication which would indicate that no cross correlation was made.

Referring to FIG. 7, the circuitry comprising the signal processing system of FIG. 1 is functionally described to facilitate a better understanding. for instance, the primary analyzer 20 may be comprised of a diastolic analysis section 20a which utilizes the f($\dot{P}$) analytical technique and a systolic analytical section 20b which utilizes the f(P) analytical technique. Similarly, the secondary analyzer is comprised of a diastolic analytical section 30a which employs the f($\dot{P}$) analytical technique and a systolic analytical section 30b which employs the f(P) analytical technique. It will be appreciated that the subscripts "a" in FIGS. 4-7 have been utilized to designate a diastolic pressure determination channel, whereas the "b" subscript has been utilized to designate a systolic pressure determination. The primary diastolic signal 22a is extended to the input of gate 60a and comparator 50a. The secondary diastolic signal 32a is extended to the input of a zone-of-acceptance definition circuit 40a which in turn has its output extended to the input of comparator 50a. The output 52a of comparator 50a is extended to the control input of gate 60a to control the output of primary diastolic pressure signal 22a through the output device 70a. The foregoing components are duplicated in a "systolic" channel with the comparable components bearing "b" subscripts. It will be appreciated that although separate components are shown in the separate channels, the separation might be one of time rather than physical components, with the diastolic and systolic determinations being made sequentially utilizing a common arrangement of logic. It will also be appreciated that instead of discrete circuitry as implied by the block diagrams in FIGS. 1,4,5,6,7, the same result can be achieved by logical operations on stored data under the command of a pre-programmed micro-processor.

Referring to FIG. 6, there is illustrated a representative diastolic pressure determining channel in which the primary diastolic pressure signal 22a is determined by analyzer 20a utilizing the f(P) technique. However now instead of there being a single secondary criterion for establishing a zone-of-acceptance, there are two such criteria, one being a diastolic value determined by analyzer 30a employing the f(P) technique and the other being a diastolic value determined by analyzer 30a' utilizing the f($\dot{P}$) technique.

The outputs of analyzers 30a and 30a' are extended via lines 32a and 32a' respectively to the inputs of zone-of-admittance definition circuitry 40a and 40a' respectively. The zone-of-admittance circuitry 40a and 40a' each define the appropriate zone-of-admittance commensurate with the particular analytical technique employed. The outputs of zone-of-admittance circuitry 40a and 40a' are extended to the inputs of comparators 50a and 50a' respectively. The primary diastolic pressure signal 22a is extended to the other input of comparator 50a. The output of comparator 50a is extended to the control input of gate 60a for controlling the passage of the primary signal 22a through the gate and via line 22a' to the other input of comparator 50a'.

The output of comparator 50a' is extended via line 52a to the control input of gate 60a'. The primary signal 22a is applied to the other input of gate 60a' for extension there through to the output device 70a when the primary signal is within both zones-of-acceptance defined by circuits 40a and 40a'. It will be appreciated that the circuitry may be so established as to provide for output of the primary signal 22a if it falls within either one or a preferred one of the two zones-of-acceptance defined by circuits 40a and 40a' respectively. A similar systolic processing channel, not shown, will provide for the output of both diastolic and systolic pressures.

Referring to FIG. 4 there is illustrated an arrangement, in a secondary diastolic signal channel employing the f(P) analytical technique, certain scaling and comparator circuitry in accordance with the invention. The diastolic analyzer 30a, during its signal analysis function, is operative to determine and temporarily store at 130a the maximum pulsatile pressure, ($P_{ac}$ max) occurring along the envelope 4. This value is then extended via line 32a to the respective inputs of 0.6 and 0.95 scaling circuits 140a and 240a respectively. The outputs of circuits 140a and 240a are $P_{ac}$ pressure values corresponding with 0.6 and 0.95 of $P_{ac}$ max. The $P_{ac}$ values determined in circuits 140a and 240a are extended to P$_{dc}$ circuits 142a and 242a respectively for conversion to the respective corresponding applied pressures (P$_{dc}$) as determined from the sum signal S extended to other inputs of circuits 142a and 242a.

Assuming the applied pressure increases with time, the determination of the applied pressures corresponding with 0.6 and 0.95 of P$_{ac}$ max. on the lower applied pressure side thereof may be determined only after the determination of P$_{ac}$ max. Therefore provision must be made either in circuits 142a and 242a or in analyzer 30a for storing applied pressure values as a function of P$_{ac}$ for essentially all applied pressures below that at which P$_{ac}$ max. occurs.

The outputs of P$_{dc}$ circuits 142a and 242a are extended to the inputs of comparators 150a and 250a respectively. The other inputs of each comparator 150a and 250a are provided by the primary diastolic pressure signal 22a. Comparator 150a provides a unity output only when primary signal 22a is greater than the P$_{dc}$ signal which corresponds with the 0.6 P$_{ac}$ max. point on the envelope 4. Similarly, the output of comparator 250a is at unity only when the primary diastolic signal 22a is less than P$_{dc}$ pressure which corresponds with 0.95 P$_{ac}$ max. point on envelope 4. The outputs of comparators 150a and 250a are respectively extended to inputs of AND gate 350a for providing a unity output signal therefrom on line 52a only when the primary signal 22a is within the defined zone-of-acceptance.

Referring now to FIG. 5 there is illustrated a secondary diastolic channel utilizing the f($\dot{P}$) analytical technique of analyzer 30a'. Analyzer 30a' determines an applied pressure substantially corresponding with diastolic pressure utilizing the f($\dot{P}$) technique, which pressure is outputed on line 32a' to respective inputs of summing circuits 140a' and 240a'. A preset signal having a value corresponding with −5 mm Hg is applied to the other input of summing circuit 140a', and a preset signal having a value of +15 mm Hg is applied to the other input of summing circuit 240a'. Thus, the output of summing circuit 140a' is an applied pressure signal corresponding with the $\dot{P}$ DIASTOLIC pressure minus 5 mm and the output of summing circuit 240a' is an applied pressure signal corresponding with $\dot{P}$ DIASTOLIC plus 15 mm. Hg. These outputs from summers 140a' and 240a' are extended to the inputs of comparator circuits extended to the inputs of comparator circuits 150a' and 250a' respectively. The primary diastolic pressure signal 22a is applied to the other input of each of comparators 150a' and 250a'. The output of comparator 150a' will be unity only if signal 22a exceeds $\dot{P}$ DIASTOLIC minus 5 mm, and the output of 250a' will be unity only if 22a is less than $\dot{P}$ DIASTOLIC plus 15 mm. The outputs of comparators 150a' and 250a' are extended to the respective inputs of AND gate 350a' such that the output 52a' thereof is unity only if the primary diastolic pressure signal 22a is within the defined zone-of-acceptance.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims and therefore intended to be embraced therein.

We claim:

1. An apparatus for producing information indicative of the physical condition of a living test subject comprising:
   means for applying a selectively changeable pressure to the test subject adjacent a blood vessel and means for measuring a fluctuating quantity proportional to a sum, said sum comprising a time dependent fluctuating component representative of the pulsatile pressure within the blood vessel, plus the selectively changeable pressure applied externally adjacent the blood vessel;
   first means responsive to said quantity in a first analytical manner for providing at least one primary signal tentatively representative of the changeable pressure applied to the living test subject;
   second means responsive to said quantity in a second analytical manner different from said first analytical manner for defining at least one respective zone-of-acceptance expressed in terms of a corresponding representation of said changeable applied pressure; and
   means for comparing a said primary signal with a respective said zone of acceptance and producing an output of said primary signal as being representative of the physical condition of the living test subject only if said primary signal is within said respective zone-of-acceptance.

2. The apparatus of claim 1 wherein said zone-of-acceptance defining means comprises means for determining a reference value in said second analytical manner and means responsive to said reference value for defining a zone-of-acceptance having a predetermined relationship to said reference value.

3. The apparatus of claim 2 wherein a said zone-of-acceptance is of greater breadth than the respective said primary signal.

4. The apparatus of claim 1 wherein said primary signal is representative of at least one of the diastolic and systolic pressures of the blood vessel.

5. The apparatus of claim 4 wherein said first analytical means provide two primary signals, said two primary signals being tentatively representative of the diastolic pressure and the systolic pressure respectively of the blood vessel and said zone-of-acceptance defining means defining two different zones-of-acceptance, one said zone-of-acceptance being for the determination of a diastolic pressure and the other said zone-of-acceptance being for the determination of a systolic pressure, and wherein said primary tentative diastolic and systolic signals are compared with said diastolic and systolic zones-of-acceptance respectively thereby to produce an output of the respective primary signal only if it is within the respective zone-of-acceptance.

6. The apparatus of claim 5 additionally including means responsive to either of said primary diastolic and systolic signals being outside its respective zone-of-acceptance for preventing output of either said primary diastolic and systolic signals.

7. The apparatus of claim 6 additionally including means responsive to either of said primary diastolic and systolic signals being outside its respective zone-of-acceptance for outputting an error indication.

8. The apparatus of claim 1 additionally including means responsive to said quantity in a third analytical manner different from said first and second analytical manners for defining at least one other zone-of-acceptance expressed in terms of said test subject physical condition, and means for comparing a said primary signal with a respective said other zone-of-acceptance and outputting said primary signal only if it is within at least one of said respective zone-of-acceptance and said respective other zone-of-acceptance.

9. The apparatus of claim 8 wherein a said primary signal is outputed only if it is within both said respective zone-of-acceptance and said respective other zone-of-acceptance.

10. The apparatus of claim 1 wherein said primary signal providing means includes means for converting said quantity into a representation of the first time derivative thereof; means for substantially maximizing said first negative time derivative of at least the fluctuating component of the quantity as a function of the applied pressure at a measurement time within the pulse, the particular applied pressure which corresponds with said maximized first time derivative comprising the diastolic pressure of the blood vessel, said particular applied pressure being said primary signal.

11. In apparatus for producing information indicative of the physical condition of a living test subject said apparatus including means for applying a selectively changeable pressure to the test subject adjacent a blood vessel and means for measuring a fluctuating quantity proportional to a sum, said sum comprising a time dependent fluctuating component representative of the pulsatile pressure within the blood vessel, plus the selectively changeable pressure applied externally adjacent the blood vessel, the improvement comprising first means responsive to said quantity in a first analytical manner for providing at least one primary signal tentatively representative of the changeable pressure applied to the living test subject;

second means responsive to said quantity in a second analytical manner different from said first analytical manner for defining at least one respective zone-of-acceptance expressed in terms of a corresponding representation of said changeable applied pressure; and means for comparing a said primary signal with a respective said zone-of-acceptance and producing an output of said primary signal as being representative of the physical condition of the living test subject only if said primary signal is within said respective zone-of-acceptance.

12. A process for producing information indicative of the physical condition of a living test subject comprising applying a selectively changeable pressure to the test subject externally adjacent a blood vessel and measuring a quantity proportional to a sum, said sum comprising a time dependent fluctuating component representative of the pulsatile pressure within the blood vessel, plus the changeable pressure applied externally adjacent the blood vessel;

analyzing said quantity in a first manner to provide at least one primary signal tentatively representative of changeable pressure applied to a living test subject;

analyzing said quantity in a second manner different from said first analytical manner to define at least one respective zone-of-acceptance expressed in terms of a corresponding representation of said changeable applied pressure; and comparing a said primary signal with a respective said zone-of-acceptance and providing an output of said primary signal as being representative of the physical condition of a living test subject only if said primary signal is within said respective zone-of-acceptance.

13. The process of claim 12 wherein said step of defining said zone-of-acceptance comprises determining a reference value in said second analytical manner and defining a said zone-of-acceptance having a predetermined relationship to said reference value.

14. The method of claim 13 wherein a said zone-of-acceptance is of greater breadth than the respective said primary signal.

15. The method of claim 12 wherein said primary signal is representative of at least one of the diastolic and systolic pressures of the blood vessel.

16. The method of claim 15 wherein said first analyzing of said quantity provides two primary signals, said two primary signals being tentatively representative of the diastolic and the systolic pressure respectively of the blood vessel and said second analyzing of said quantity defines two different zones-of-acceptance, one said zone-of-acceptance being for the determination of a diastolic pressure and the other said zone-of-acceptance being for the determination of a systolic pressure, and comparing said primary tentative diastolic and systolic signals with said diastolic and systolic zones-of-acceptance respectively thereby producing an output of the respective primary signal only if it is within the respective zone-of-acceptance.

17. The method of claim 16 additionally including the step of preventing output of either of said primary diastolic and systolic signals if either of the respective primary diastolic and systolic signals is outside its respective zone-of-acceptance.

18. The method of claim 17 including the additional step of outputting an error indication if either of said primary diastolic and systolic signals is outside its respective zone-of-acceptance.

19. The method of claim 12 additionally including the step of analyzing said quantity in a third manner different than said first and second analytical manners to define at least one other zone-of-acceptance expressed in terms of said test subject physical condition, and comparing a said primary signal with a respective said other zone-of-acceptance and outputting said primary signal only if it is within at least one of said respective zone-of-acceptance and said respective other zone-of-acceptance.

20. The method of claim 19 including outputting a said primary signal only if it is within both said respective zone-of-acceptance and said respective other zone-of-acceptance.

21. The method of claim 12 wherein said analyzing in said first manner comprises converting said quantity into a representation of the first time derivative thereof, substantially maximizing said first time derivative of at least the fluctuating component of the quantity as a function of the applied pressure at a measurement time within the pulse, and providing the applied pressure which corresponds with said maximized first time derivative as said primary signal, said primary signal comprising the diastolic pressure of the blood vessel.

22. In a process for producing information indicative of the physical condition of a living test subject including applying a selectively changeable pressure to the test subject externally adjacent a blood vessel and measuring a quantity proportional to a sum, said sum comprising a time dependent fluctuating component representative of the pulsatile pressure within the blood vessel, plus the changeable pressure applied externally adjacent the blood vessel, the improvement comprising:

analyzing said quantity in a first manner to provide at least one primary signal tentatively representative of a changeable pressure applied to a living test subject;

analyzing said quantity in a second manner different from said first analytical manner to define at least one respective zone-of-acceptance expressed in terms of a corresponding representation of said changeable applied pressure; and comparing a said primary signal with a respective said zone-of-acceptance and providing an output of said primary signal as being representative of the physical condition of a living test subject only if said primary signal is within said respective zone-of-acceptance.

* * * * *